United States Patent [19]

Eckhoff et al.

[11] Patent Number: 4,703,647

[45] Date of Patent: Nov. 3, 1987

[54] APPARATUS FOR MEASURING GRAIN HARDNESS

[75] Inventors: Steven R. Eckhoff; Darrell Oard; Arthur B. Davis; Kieth C. Behnke, all of Manhattan, Kans.

[73] Assignee: Kansas State University Research Foundation, Manhattan, Kans.

[21] Appl. No.: 883,970

[22] Filed: Jul. 10, 1986

[51] Int. Cl.$^4$ ............................................... G01N 3/40
[52] U.S. Cl. .......................................... 73/81; 73/78; 83/411 A; 241/6
[58] Field of Search ................. 73/78, 81, 866, 7; 83/411 R, 411 A, 435; 198/380, 391, 479.1; 241/6, 7, 30, 278 R

[56] References Cited

U.S. PATENT DOCUMENTS

| | | | |
|---|---|---|---|
| 2,226,600 | 12/1940 | Eddington | 73/78 X |
| 2,839,917 | 6/1958 | Webster | 73/81 |
| 3,264,866 | 8/1966 | Bouschart et al. | 73/78 |
| 3,511,078 | 5/1970 | Rajkai | 73/866 X |
| 3,592,362 | 7/1971 | Kane | 73/7 X |
| 4,472,960 | 9/1984 | Motoyama et al. | 73/866 X |

OTHER PUBLICATIONS

"Determination of Hardness in Wheat Mixtures, Part II. Apparatus for Automated Measurement of Hardness of Single Kernels"; *Cereal Chemistry*, 34 page copy of article therein; published 1985; F. S. Lai et al.

*Primary Examiner*—Tom Noland
*Attorney, Agent, or Firm*—Tilton, Fallon, Lungmus & Chestnut

[57] ABSTRACT

A grain hardness tester which includes a rotating plate equipped with a plurality of openings arranged in a circle around the plate periphery, a grain feeder adapted to dispense grains singly and sequentially into the openings, the plate being equipped with a peripheral slot communicating with the openings, a disc positioned in the slot and adapted to engage the grains sequentially and a load cell and microprocessor operably associated with the disc for reporting the force of encounter of the disc with a grain kernel.

10 Claims, 6 Drawing Figures

APPARATUS FOR MEASURING GRAIN HARDNESS

BACKGROUND OF THE INVENTION

The development by Kansas State University agronomists of a wheat variety called Arkan, which looks like a soft wheat but bakes and mills like a hard wheat, has spurred interest in developing an objective means of delineating hard from soft wheat. The present method of classification used by the Federal Grain Inspection Service (FGIS) is visual, based on shape and color characteristics of traditional hard and soft wheats. Plant breeders have traditionally found that the shape and color characteristics that denote a hard wheat tend to be genetically transferred with the end use characteristics of baking, hardness, and milling that constitute hard wheat. However, as cross-breeding between hard and soft wheat continues the two sets of traits do not necessarily transfer together. The result is hard wheats that look like soft wheats and soft wheats that look like hard wheats. Because some of these new varieties have desirable insect resistance, drought resistance, or yield potential, it is imperative that a rapid method be developed to delineate hard from soft wheat based on end-use characteristics rather than on visual characteristics.

Bulk testing methods such as time to grind, resistance to grinding, particle size index and near infrared reflectance can be used to delineate hard from soft samples but are not sensitive enough to identify the degree of adulteration in blended samples. Federal regulations allow a maximum of 5% adulteration of a wheat class with other wheat classes. Beyond the 5% level the end use quality of the wheat is affected.

Our approach to the problem is to measure the hardness of individual kernels within a bulk sample. By measuring a large enough number of individual kernels a good estimation on the level of adulteration can be achieved. This approach has also been chosen by Lai, et al (1985), Determination of Hardness in Wheat Mixtures., working on the problem at the USDA Grain Marketing Research Laboratory in Manhattan, Kans. They developed an instrument which singularizes the wheat kernels and crushes them with a rounded probe at the rate of 15 kernels per minute. They investigated six parameters of the breakage event to determine which parameter gave best delineation between hard and soft wheat. They determined the ratio of the first valley to the first peak on the breakage event curve gave the best separation between hard and soft wheat. Tested using samples of known adulteration levels, the instrument was 90% accurate in determining the level of adulteration.

SUMMARY OF INVENTION

The inventive instrument is constructed to singularize and orient the wheat kernels so that they can be sliced or crushed by rotary means such as a sharp or blunt disc. The force experienced by the rotary means is measured by a load cell and it is this recorded breakage event which contains the information necessary to determine if the kernel is a hard or soft kernel. The basic premise the instrument operates on is that hard kernels are harder or more brittle than the softer or more ductile soft kernels.

The invention is described in conjunction with the accompanying drawing in which.

DETAILED DESCRIPTION

Operation Generally

Figure 4:
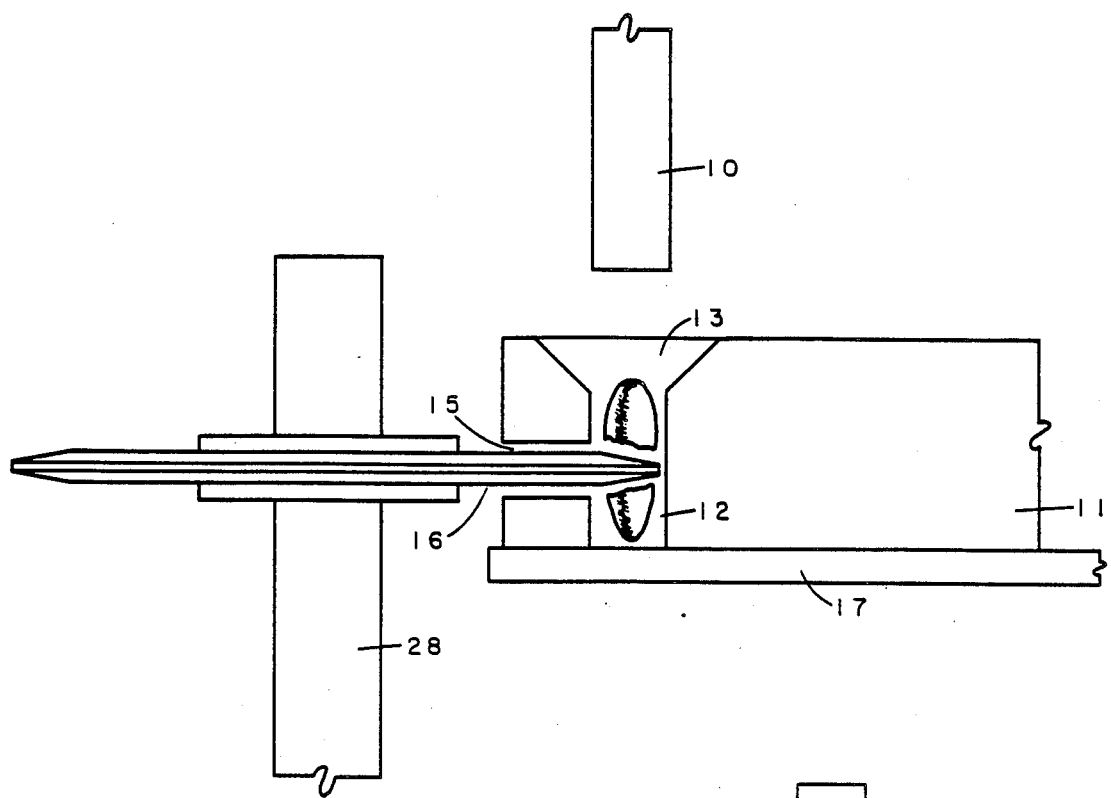
FIG. 4 is a fragmentary enlarged rear elevational view.

Singularization of the kernels is achieved using a vibrating feeder mechanism off of a seed counter. The feeder also aligns the kernels so that they will feed into a copper drop tube, see FIG. 1 at 10, which gravity feeds the kernels to a rotating plate 11 revolving at 6 rpm. The plate contains 48 closely aligned holes that have a 45° beveled entrance 13. A cross-sectional diagram of one of the holes 13 is shown in FIG. 4. The beveled area acts as a funnel which catches the kernel as it falls from the drop tube.

About 40–50% of the kernels which fall from the drop tube drop directly into the hole. The remaining 50–60% of the kernels end up laying cross-ways in the beveled funnel area or are only partially down in the hole. The blast of air from the air positioner 14 shown in FIG. 3 lifts the kernel that is not firmly in the hole and directs it into the hole. The air positioner works so well that only rarely does a kernel which drops out of the drop tube not end up properly placed in a hole.

Figure 4A:
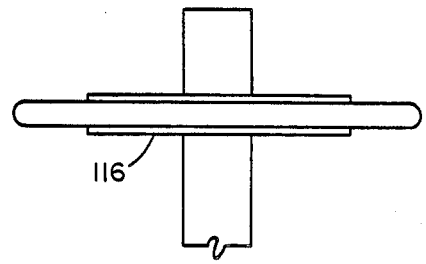
FIG. 4A is a fragmentary rear elevational view of a modified form of a rotary disc used in the invention.

The disc groove 15 shown in FIG. 4 extends all the way around the plate and has a depth that goes nearly to the back of the holes. The depth is adjustable through adjustment of the load cell rod 34 and movement of the bearings 30 and 31. The illustrated rotary knife 16 sits in this groove and as the kernels are rotated to the knife, the knife slices them through. The edge of the rotary knife is sharp to get a smooth cut. Alternatively, the blunt disc 116 seen in FIG. 4A can be employed which provides a crushing action.

After being sliced, the kernels are cleaned from the holes by two means. The first is gravity. The stationary plate 17 does not cover the bottom of the rotating plate 11 in this area and kernels can fall out of the hole. The second method is by blasts of compressed air which removes fine stuck particles from the hole and the knife groove. Clean-out by this method is very good although occasionally a kernel will lodge in the hole and will require mechanical means for removal.

Figure 5:
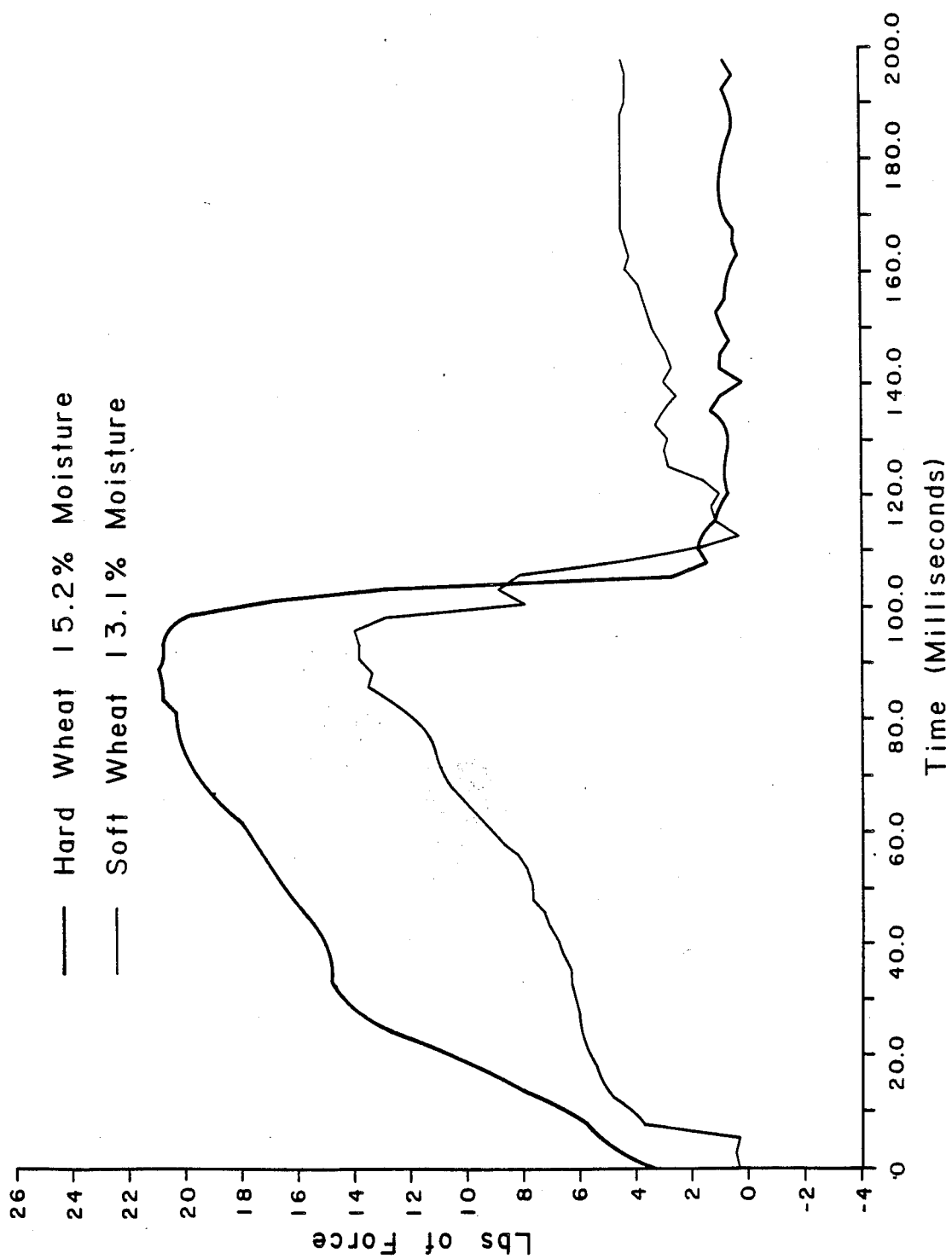
FIG. 5 is a chart depicting performance of the invention.

The rotary knife is attached to a 50 lbf load cell. Forces experienced by the knife are monitored by the load cell. Load cell values are sampled every millisecond and values recorded by an IBM-PC for analysis. FIG. 5 shows a representative response of the load cell to a breakage event.

Structured Details

1. Rotating Plate

Figure 1:
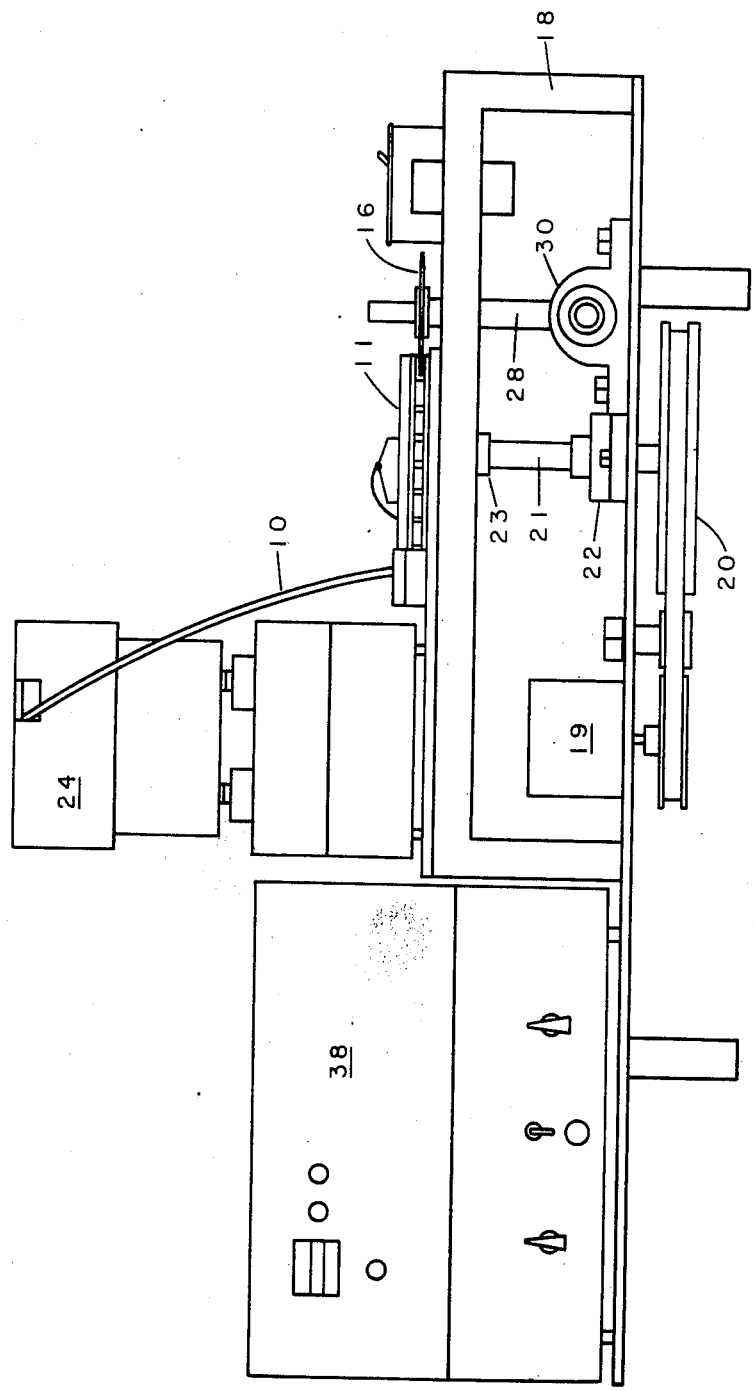
FIG. 1 is a front elevational view of the inventive instrument.

Referring first to FIG. 1, the number 18 designates generally a frame or pedestal which carries the operating elements. A motor 19 is carried by the frame 18 and is coupled by a pulley and belt drive 20 to a vertical shaft 21 to which the rotating plate 11 is fixed. The shaft 21 is journaled in suitable bearings at 22 and 23.

Figure 3:
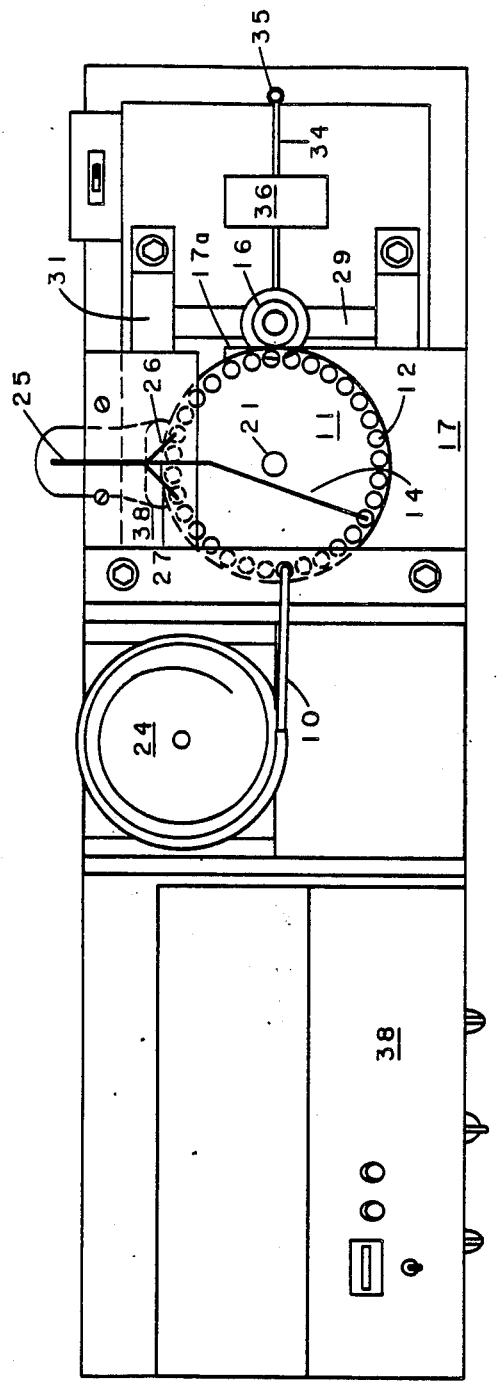
FIG. 3 is a top plan view.

As seen in FIG. 3, the plate 11 is equipped with a plurality of holes 12 which are arranged in a circle. Still referring to FIG. 3, the numeral 24 designates a grain feeder arranged to dispense individual grains sequentially. A suitable grain feeder can be obtained commercially from FMC Corporation-Syntron Division located at Homer City, Pa., Model No. EB051. The grain feeder 24 delivers the grains sequentially to the previously mentioned drop tube 10.

2. Grain Feeder

As illustrated in FIG. 3, a grain enters an opening in the rotating plate 11 at 9:00 o'clock and encounters the air blast from positioner 14 at about 7:00 o'clock. Thereafter the grain is engaged by rotary knife 16 at the 3:00 o'clock position. Removal is effected by gravity and another air blast at about 12:00 o'clock.

A compressed air line 25 supplies air to the positioner 14 and removal branch lines 26, 27. The stationary plate 17 extends to most but not all of the periphery of the rotating plate 11. More particularly it terminates short of the removal area, as at 17a. A plate of plexiglass 38 is affixed above the removal area to direct broken kernel particles downward into the collection area.

3. Rotary Disc

Figure 2:
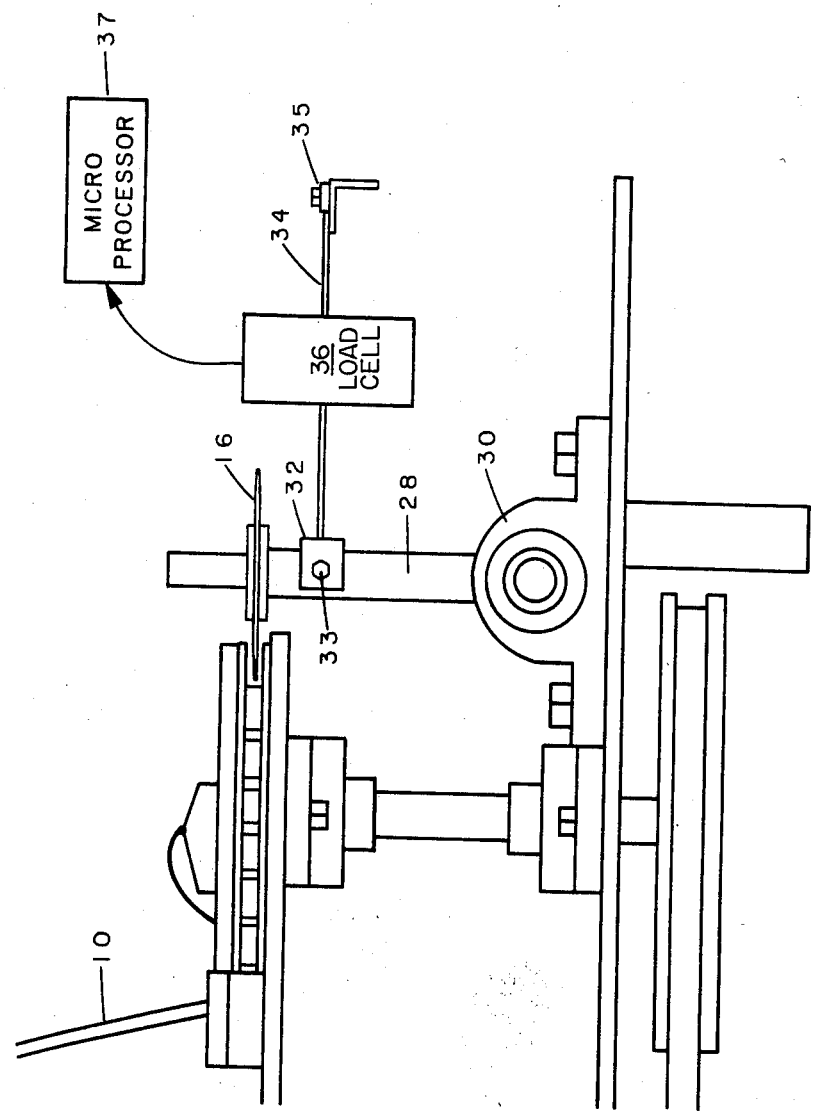
FIG. 2 is a fragmentary enlarged front elevational view and partially schematic.

Referring now to FIG. 2, the disc 16 is rotatably mounted on a vertical shaft 28. It is not driven but is freely rotatable on a suitable bearing (not shown). The shaft 28 at its lower end is fixed to a horizontal shaft 29 (see FIG. 3). The shaft 29 in turn is rotatably mounted within bearings 30, 31. Thus the vertical shaft 28 is adapted to pivot back and forth through a small vertical arc in response to the resistance encountered in slicing into or crushing the grain kernel.

4. Sensing/Reporting Means

The pivotal movement of the vertical shaft 28 is transmitted through a yoke 32 (see FIG. 2). The yoke 32 is pivotally mounted on the shaft 28 by a pin 33. A rod 34 (compare FIGS. 2 and 3) is fixed at one end to the yoke 32 and at the other end fixed to a part of the frame as at 35.

Interposed between the yoke 32 and the fixed part 35 is a load cell 36 which advantageously can be of the manufacture of Eaton Corporation located at Troy, Mich. and being Model No. 3108 and which measures the strain exerted by the engagement of the disc with the kernel.

The output signal from the load cell 36 is delivered to a micro processor 37 also illustrated schematically in FIG. 2. This is advantageously provided as part of the control console 38 (compare the left hand portions of FIGS. 1 and 3). The console includes a micro processor manufactured by Zenith Corporation, located in Chicago, Ill. and having Model No. 151.

With the inventive instrument, a higher speed operation is achieved in that the physical characteristics of more kernels can be determined in a given period of time. For example, prior art devices could crush only 15 grains per minute whereas the invention has operated successfully at 200 grains per minute and is expected to function satisfactorily up to 1000 grains per minute.

It will be appreciated that through suitable sizing of the openings 12, the inventive apparatus can test the hardness of other grains. In rice, it is advantageously employed to determine milling characteristics, viz., how to handle, dry, etc. in processing. In barley, hardness relates to quality. In corn, it relates to durability in storage and handling—the hard variety is more durable.

We claim:

1. Apparatus for measuring the hardness of grains comprising a frame providing a stationary plate-like pedestal,
    a plate mounted on said pedestal for rotation in a horizontal plane and equipped with a plurality of vertically-extending grain receiving openings arranged in a circle and sized for the receipt of individual grains, means on said frame for rotating said plate, said plate having a radially inwardly directed slot extending around the periphery thereof and communicating with said openings,
    a drop tube on said frame for delivering grains sequentially into said openings,
    disc means on said frame adjacent said plate and having a portion positioned within said slot for applying a force to grains sequentially, and means operably associated with said disc and frame for reporting the magnitude of the force.

2. The apparatus of claim 1 in which said drop tube and said disc means are positioned on said frame a spaced arcuate distance apart, and air blast means on said frame intermediate thereof is used for repositioning a grain in its receiving opening.

3. The apparatus of claim 1 in which said reporting means includes a load cell for sensing and recording the magnitude of force required to cause said disc means to penetrate the grain a predetermined distance.

4. The apparatus of claim 3 in which said disc means has a sharpened periphery.

5. The apparatus of claim 3 in which said disc means has a blunt periphery.

6. The apparatus of claim 1 in which each opening has an upwardly facing frusto-conical entrance.

7. Apparatus for measuring the hardness of grains comprising a frame providing a stationary plate-like pedestal, a plate rotatably mounted on said pedestal and equipped with a plurality of grain receiving openings arranged in a circle and sized for the receipt of individual grains, means on said frame for rotating said plate, a drop tube on said frame for delivering grains sequentially into said openings, disc means on said frame adjacent said plate for applying a force to grains sequentially and means operably associated with said disc and frame for reporting the magnitude of the force, said rotatably mounted plate being equipped with a radially directed peripheral slot communicating with said openings, said disc means being positioned in said slot.

8. The apparatus of claim 7 in which said reporting means includes a load cell adapted to report the force encountered by said disc in engaging a discrete grain.

9. Apparatus for measuring the hardness of grain kernels including a frame, a circular plate rotatably mounted on said frame, means on said frame for rotating said circular plate about its central axis, a plurality of openings extending axially through said plate adjacent the periphery of said plate, each opening having a beveled upper entrance, a grain feeder on said frame for singularizing grains and delivering the same to a first location in the arcuate path of travel of said openings, said plate having a radially inwardly directed slot extending around the periphery thereof and communicating with said openings, a disc rotatably mounted on said frame and having a portion positioned within said slot, said disc being located at a second location which is a spaced arcuate distance from said first location, stationary plate means closing the bottoms of said openings between and including said first and second locations, and air blast means for reorienting grains in said openings mounted on said frame for blast delivery while a grain is traveling from said first location to said second location.

10. The apparatus of claim 9 in which said air blast means provides another air blast into said openings on the path of travel of grains from said second location toward said first location to assist in grain removal.

* * * * *